United States Patent [19]

Martan et al.

[11] Patent Number: 4,916,103
[45] Date of Patent: Apr. 10, 1990

[54] PREPARATION OF A CATALYTICALLY ACTIVE COMPOSITION FOR THE GAS PHASE OXIDATION OF PROPYLENE TO ACROLEIN AND ACRYLIC ACID

[75] Inventors: Hans Martan, Frankenthal; Matthias Schwarzmann, Limburgerhof; Karl-Heinz Boehning, Darmstadt; Heinz Dreyer, Ludwigshafen, all of Fed. Rep. of Germany

[73] Assignee: BASF Aktiengesellschaft, Ludwigshafen, Fed. Rep. of Germany

[21] Appl. No.: 275,974

[22] Filed: Nov. 25, 1988

[30] Foreign Application Priority Data

Nov. 27, 1987 [DE] Fed. Rep. of Germany ....... 3740271

[51] Int. Cl.⁴ ................. B01J 23/78; B01J 23/84; B01J 23/88; B01J 27/18
[52] U.S. Cl. .................................... 502/212; 502/311
[58] Field of Search .......................... 502/212, 311

[56] References Cited

U.S. PATENT DOCUMENTS

| | | | |
|---|---|---|---|
| 3,746,657 | 7/1973 | Miller et al. | 252/437 |
| 4,052,450 | 10/1977 | Krabetz et al. | 260/533 N |
| 4,168,246 | 9/1979 | Li et al. | 252/437 |
| 4,190,608 | 2/1980 | Grasselli et al. | 260/604 R |
| 4,212,766 | 7/1980 | Brazdil et al. | 502/212 X |
| 4,267,386 | 5/1981 | Vanderspurt et al. | 568/480 |
| 4,272,637 | 6/1981 | Yamamoto et al. | 568/780 |
| 4,306,090 | 12/1981 | Kirch et al. | 568/481 |
| 4,537,874 | 8/1985 | Sato et al. | 502/311 |

FOREIGN PATENT DOCUMENTS 1282949 7/1972 United Kingdom .

Primary Examiner—W. J. Shine
Attorney, Agent, or Firm—Oblon, Spivak, McClelland, Maier & Neustadt

[57] ABSTRACT

A catalytically active composition for the gas phase oxidation of propylene to acrolein and acrylic acid, of the general formula

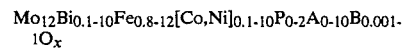

where A is arsenic, antimony, tin, thallium, tungsten, an alkaline earth metal, zinc and/or chromium, B is at least one of the metals sodium, potassium, rubidium, cesium and/or indium and X is the number determined by the atomic valences of the individual elements, is prepared by introducing all or some of the iron and molybdenum in the form of dried pulverulent iron molybdate gel into an aqueous solution or suspension of the other constituents and gelating the mixture by stirring and possibly heating, then comminuting, drying at elevated temperatures and finally calcining.

1 Claim, No Drawings

PREPARATION OF A CATALYTICALLY ACTIVE COMPOSITION FOR THE GAS PHASE OXIDATION OF PROPYLENE TO ACROLEIN AND ACRYLIC ACID

The present invention relates to a specific process for preparing a catalytically active composition for the gas phase oxidation of propylene to acrolein and acrylic acid which is based on oxides or mixed oxides of molybdenum, bismuth, iron and other metallic components customary for this purpose.

Catalytically active compositions of the general formula $$Mo_{12}Bi_{0.1-10}Fe_{0.8-12}[Co,Ni]_{0.1-10}P_{0-2}A_{0-10}B_{0.001-10}O_x$$

where A is arsenic, antimony, tin, thallium, tungsten, an alkaline earth metal, zinc and/or chromium, B is at least one of the metals sodium, potassium, rubidium, cesium and/or indium and X is the number determined by the atomic valences of the individual elements, are known for example from German Laid-Open Application DOS No. 3,338,380, GB Pat. No. 1,437,235 (O.Z.0050/39443) and DE Pat. No. 2,229,358. They are in general prepared by mixing water-soluble salts of the constituents in an aqueous medium, evaporating the water and calcining at from 400° to 650° C. In the process of German Laid-Open Application DOS No. 3,338,380, the bismuth and tungsten to be included in the catalytically active composition can be added to the mixture of the water-soluble salts of the other components and in this way a comparatively low reaction temperature for the gas phase oxidation of propylene can be obtained together with a simultaneous increase in the total yield of acrolein and acrylic acid.

The water can for example be evaporated from the aqueous mixture of the salts of the catalyst components while the mixture is being stirred, but in this case the individual components precipitate out of the solution in order of solubility products, and in this way it is impossible to obtain a homogeneous mixture of the dried material, even if this material is in addition substantially ground. Even if the aqueous mixtures of the salts of the components are spray-dried as described for example in DE Pat. No. 2,229,358, problems occur due to clogging of the nozzles, caking of the product to the walls and clumping, despite the observance of many boundary conditions, and even if drying has gone according to plan the spray-dried products must frequently be agglomerated into larger particles to eliminate dusting and improve handling during further processing.

It is an object of the present invention to provide a process for preparing such a catalytically active composition in which the components have been dispersed especially homogeneously and which ensures simple handling.

We have found that this object is achieved advantageously with a process for preparing, for the gas phase oxidation of propylene to acrolein and acrylic acid, a catalytically active composition of the general formula $$Mo_{12}Bi_{0.1-10}Fe_{0.8-12}[Co,Ni]_{0.1-10}P_{0-2}A_{0-10}B_{0.001-10}O_x$$

where A is arsenic, antimony, tin, thallium, tungsten, an alkaline earth metal, zinc and/or chromium, B is at least one of the metals sodium, potassium, rubidium, cesium and/or indium and X is the number determined by the atomic valences of the individual elements, by mixing water-soluble salts of the constituents in an aqueous medium, evaporating the water and calcining at from 400° to 650° C., when a dried pulverulent iron molybdate gel ($Fe(MoO_4)_3$) is added to an aqueous solution or suspension of water-soluble salts of the other constituents customary for this purpose, including any excess of iron or molybdenum salt beyond the amount introduced with the iron molybdate, the mixture is rigidified into a gel by stirring and possibly heating, and the gel is comminuted and dried at an elevated temperature and then calcined.

The dried pulverulent iron molybdate gel can be pretreated in a conventional manner, for example as described in GB Pat. Nos. 1,282,949 and 1,282,950. In practice the pretreatment comprises gradually adding an iron nitrate solution to a cooled solution of ammonium heptamolybdate with stirring and continuing with the stirring until the initial precipitate dissolves and the then clear solution rigidifies to form a greenish gel. This gel is dried to give a reddish brown powder.

The dried pulverulent iron molybdate gel preferably has an average particle size of from 10 μm to 2 mm and, in the process according to the invention, is in general added at room temperature to the aqueous solution or suspension of the other components with stirring, for which a speed of from 20 to 200 rpm with a customary vane stirrer has proved particularly useful.

To prepare the aqueous solution or suspension of the other catalyst components, it is possible to use the water-soluble salts customary for this purpose, for example nitrates, carbonates, formates, acetates and ammonium salts.

If more than 8 moles of iron per 12 moles of molybdenum are used for the catalytically active composition, the excess is added to the aqueous solution of the other components in the form of the water-soluble iron salt customarily used for this purpose, for example iron(III) nitrate or carbonate. If the catalytically active composition is to have an iron content of below about 7.5 moles of iron for every 12 grammoles of molybdenum, the excess amount of molybdenum is added in the course of the preparation of the aqueous solution of the other components in the form of the molybdenum compounds customary for this purpose, for example ammonium heptamolybdate or molybdenum trioxide, and also ammonium dimolybdate In other words, if the catalyst is to contain for example 6 moles of iron for every 12 moles molybdenum, the total quantity of iron is added in the form of the iron molybdate gel and 3 moles of molybdenum are added in the form of the water-soluble molybdenum compound. After the pulverulent dried iron molybdate has been added to the aqueous solution or suspension of the other components with stirring a granular gel forms, if necessary after slight heating for example from 25° to 90° C., in particular from 30° to 50° C., which holds the catalyst components in optimal homogeneous distribution. The granular gel can be dried for example in a rotary tube oven or in a fluidized bed in general at from 90° to 35° C., preferably at from 110° to 120° C., if necessary in an airstream. The result then obtained is a finely granular composition which is readily grindable down to an average particle size of from 10 to 300 μm. The pulverulent catalytically active composition obtained can be used in a conventional manner with or without pulverulent carrier materials, such as silicon dioxide, to obtain molded catalyst particles, for example small cylinders from 3 to 7 mm in diameter and also from 3 to 7 mm in length, or for coating balls of carrier material from 2 to 7 mm in diameter or even rings of carrier material.

The catalytically active compositions prepared by the novel process and the catalysts produced therefrom can be used with advantage for the gas phase oxidation of olefins, in particular propylene and also purpose to give the corresponding $\alpha,\beta$-monoolefinically unsaturated aldehydes, in particular acrolein. In general this gas phase oxidation is carried out at from 250° to 450° C., in particular at from 300° to 380° C., under pressures of from 1.0 to 3, in particular from 1.1 to 1.8 bar, the composition of the gas mixture being within the range from 2 to 15, in particular from 5 to 10, by volume of propylene.

It is an advantage of the novel process for preparing the catalytically active compositions that a particularly homogeneous distribution of the individual catalyst components is obtained.

On using the novel catalytically active compositions for the gas phase oxidation of olefins, in particular propylene, an improved selectivity and a distinctly improved activity are obtained.

In the Examples below, parts and percentages are by weight, unless otherwise stated.

EXAMPLE 1

(a) A catalytically active composition of the general formula:

$Mo_{12}Bi_{1.2}W_{2.4}Co_{4.8}Fe_{0.8}Si_{1.6}K_{0.05}O_x$ is prepared as follows:

476.70 g of ammonium heptamolybdate are dissolved by heating in distilled water admixed with 11.25 ml of 1N KOH. After the solution has cooled down, 79.75 g of $NH_4NO_3$-containing iron molybdate, 349.23 g of cobalt nitrate, 209.23 g of bismuth tungstenate $(Bi_{1.2}W_{2.4}O_x)$ and 80.11 g of a 30% strength silica sol solution are added in succession with stirring. Stirring of the suspension is continued until, after from 10 to 15 minutes, it consolidation into a granular paste. This paste is dried at 110° C. in a porcelain dish in the course of 16 hours and then chipped into a particle size of from 0.71 to 1.60 mm. The chips are calcined in a rotary tube at 450° C. for 6 hours (b) 40 parts of the chips prepared as described in (a) are introduced into a tube 0.8 cm in clear diameter and 1.0 m in length, and a mixture of propylene/air/nitrogen/water in a ratio of 1:9:10:2 is passed over at 360° C. A flow velocity of 76 parts volume/hour give a yield of acrolein plus acrylic acid of 90.6 mol-%, based on the propylene used.

COMPARATIVE EXAMPLE 1

(a) A catalyst of the composition specified in Example 1a is prepared as follows:

An aqueous solution of 211.9 g of ammonium heptamolybdate and 5 ml of 0.1N KOH is introduced initially and heated to 40° C. A solution of 139.69 g of cobalt nitrate and 32.32 g of iron nitrate is added continuously. Finally, 19.79 g of a 48.6% strength silica sol solution are added.

The suspension is subsequently spray-dried, 180 g of a spray-dried product having a particle size <0.160 mm are mixed with 47.48 g of bismuth tungstenate, and the mixture is kneaded with water.

The kneaded material is dried for 16 hours and chipped to a particle size of from 0.71 to 1.60 mm.

The chips are calcined in a rotary tube at 450° C. for 6 hours.

The catalyst is then tested at 360° C. as described in Example (1b), giving a yield of acrolein (plus acrylic acid) of not more than 85 mol-%.

EXAMPLE 2

(a) A catalyst of the general formula $Mo_{12}Bi_{0.98}Fe_{1.98}Ni_{6.34}Zn_{1.95}K_{0.05}Na_{0.15}Si_{10}O_x$ is prepared as follows:

66.76 g of ammonium heptamolybdate are dissolved in 67 g of water by heating. After the solution has cooled down, 76.82 g of nickel nitrate and a nitric acid solution of 21.24 g of zinc nitrate and 19.85 g of bismuth nitrate are added with stirring. Finally, 39.91 g of $NH_4NO_3$-containing iron molybdate, 2.08 ml of 1N KOH and 51.52 g of a 48.6% strength silica sol solution are added. Following a brief period of stirring and slight heating, the suspension consolidates to become a granular paste. This paste is dried in a porcelain dish at 110° C. for 16 hours and is chipped down to a particle size of from 0.71 to 1.60 mm, and the chips are calcined in air in a rotary tube at 580° C. for 2 hours.

(b) The catalyst is tested as described in Example (1b), giving a yield of acrolein (plus acrylic acid) of 87 mol-% at 360° C.

EXAMPLE 3

(a) A catalyst of the general formula $Mo_{12}Bi_{0.98}Ni_{8.29}Fe_{1.95}Si_{10}K_{0.05}Na_{0.15}O_x$ is prepared as described in Example 2, except that the zinc nitrate is replaced by an increased amount of nickel nitrate, namely a total of 100.45 g of nickel nitrate.

(b) The catalyst is tested as described in Example 1b), giving a yield of acrolein (plus acrylic acid) of 81 mol-% at 360° C. for a gas speed of 80 parts by volume/hour.

We claim:

1. A process for preparing, for the gas phase oxidation of propylene to acrolein and acrylic acid, a catalytically active composition of the general formula $Mo_{12}Bi_{0.1-10}Fe_{0.8-12}M_{0.1-10}P_{0-2}A_{0-10}B_{0.001-1}O_x$ wherein A is arsenic, antimony, tin, thallium, tungsten, an alkaline earth metal, zinc and/or chromium, B is at least one of the metals sodium, potassium, rubidium, cesium and/or indium, M is Ni, Co or a combination thereof, and x is the number determined by the atomic valences of the individual elements, by mixing salts of the constituents in an aqueous medium, evaporating the water and calcining at from 400° to 650° C., wherein a dried pulverulent iron molybdate gel $(Fe(MoO_4)_3)$ is added to an aqueous solution or suspension of water-soluble salts of the other constituents customary for this purpose, including any excess of iron or molybdenum salt beyond the amount introduced with the iron molybdate, the mixture is rigidified into a gel by stirring and possibly heating, and the gel is constituted and dried at an elevated temperature and then calcined.

* * * * *